United States Patent [19]

Hoy, Jr.

[11] Patent Number: Plant 6,669

[45] Date of Patent: Mar. 14, 1989

[54] ROSE PLANT SEEDLING NAMED CHARADE

[75] Inventor: Lowell L. Hoy, Jr., Richmond, Ind.

[73] Assignee: Joseph H. Hill Company, Richmond, Ind.

[21] Appl. No.: 61,670

[22] Filed: Jun. 15, 1987

[51] Int. Cl.[4] ..... A01H 5/00

[52] U.S. Cl. ..... Plt./28

[58] Field of Search ..... Plt./28, 29

*Primary Examiner*—Robert E. Bagwill

*Attorney, Agent, or Firm*—Charles W. Rummler

[57] ABSTRACT

A new floribunda rose variety distinguished by its abundant and continuous production of well-formed flowers of relatively small size and a bright cardinal red color which remains unchanged for the life of the fully opened bloom and which persists as a cut flower for up to ten days under normal conditions of vase keeping; this new plant is also distinguished by its free and vigorous growth habit and by its very high wintertime productivity during greenhouse culture.

1 Drawing Sheet

BACKGROUND OF THE NEW PLANT

My new variety of red floribunda rose originated as a seedling resulting from breeding efforts carried on by me at Richmond, Ind., with the object of producing rose plants having blooms of red color and high productivity, and a free and vigorous growth habit with blooms of attractive form and improved keeping qualities. The crossing to produce this new plant was done by me in the Spring of 1981 with the first flower occurring in the Fall of 1982, this crossing having been done by me in greenhouse at Richmond, Ind. The improved and favorable characteristics of this new plant led to my asexual propagation of the plant by budding at Richmond, Ind., and further propagation under my direction was done through several successive generations by budding at Richmond, Ind., and at Pleasanton, Calif., all of which has demonstrated that the distinctive features of this new plant hold true from generation to generation and appear to be firmly fixed.

DESCRIPTION OF THE DRAWING

This new variety of cardinal red rose plant is illustrated by the accompanying photographic drawing which shows, in full color, a newly opened and a three-day opened flower, several stages of bud opening, and specimens of plant parts including petals of newly-opened and mature blooms, the colors shown being as nearly true as can be obtained by professional photographic procedures.

DESCRIPTION OF THE NEW PLANT

The following is a detailed description of my new rose plant with designations of color according to Koster's Color Guide (K) and the Horticultural Colour Chart (HCC) published in 1966 by The Royal Horticultural Society of London, England, the data being derived from observations made in January 1987 in greenhouse in Richmond, Ind.

THE PLANT

Origin: Seedling.

Parentage:

*Seed parent.*—'Cindy', U.S. Plant Pat. No. 3,910.

*Pollen parent.*—'Sassy', U.S. Plant Pat. No. 4,559.

Classification:

*Botanic.*—Polyantha.

*Commercial.*—Floribunda — cut flower.

Form: Bush.

Habit: Upright and much branched.

Growth: Free, vigorous and with medium strong canes.

Main stems:

*Color.*—Spinach Green, 0960/1 (HCC).

*Thorns.*—Few, of medium length, straight and with a short, narrow base. Color: Lilac, Plate No. 48 (K).

*Prickles.*—Few in number. Color: Bistre, Plate No. 93 (K).

Branches:

*Color.*—Spinach Green, 0960/3 (HCC).

*Thorns.*—Several, of medium length, straight and with a narrow, short base. Color: Bistre, Plate No. 93 (K).

*Prickles.*—Very few in number. Color: Bistre, Plate No. 93 (K).

New shoots:

*Color.*—Fern Green, 0862 (HCC).

*Thorns.*—Few, short and straight, with a short, narrow base. Color: Chrysanthemum Crimson, 824/3 (HCC).

Foliage:

*Quantity.*—Moderately abundant and of medium size.

*Leaves.*—Shape: Odd pinnate, with three to seven leaflets.

*Shape of leaflets.*—Ovoid with acuminate apex, obtuse base and serrate margins.

*Aspect.*—Moderately glossy.

*Color.*—Mature Leaf: Upper Surface — Spinach Green, 0960 (HCC). Under Surface — Cedar Green, Plate No. 80 (K). Young Leaf: Upper surface — Spinach Green, 0969/2 (HCC) shaded with Chrysanthemum Crimson, 824/2 (HCC). Under surface — Cedar Green, Plate No. 80 (K) shaded with Chrysanthemum Crimson, 824/2 (HCC).

*Rachis.*—Medium heavy, grooved and hairy on upper side and almost smooth on the under side.

*Stipules.*—Of medium length and width with points which turn out at an angle of more than 45° and recurve toward the stem.

THE BUD

Before calyx breaks:

*Size.*—Medium small.

*Form.*—Short pointed with a conspicuous neck, with foliaceous appendages on the surface of the bud, and with slender foliaceous parts extending beyond the tip of the bud a distance equal to about one-fourth or more of the bud length.

*Calyx color.*—Pod Green, 061 (HCC).

As the calyx breaks:

*Color.*—Outside of the Petals: Cardinal Red, 822/1 (HCC).

As the first petal opens:

*Bud size.*—Medium small. Form: Short pointed.

*Color of petals.*—Outside and Inside: Cardinal Red, 822/1 (HCC).

Bud opening: In greenhouse, the bud opens up well.

Sepals:

*Persistence.*—Permanent.

*Length.*—Medium.

*Shape.*—Spear-shaped and recurved.

*Color.*—Inside — Scheeles Green, 860/3 (HCC), with white fuzz. Outside — Scheeles Green, 860/3 (HCC), tinted with Scheeles Green, 860 (HCC).

Peduncle:

*Character.*—Of medium length and diameter, strong and erect.

*Bark.*—Slightly rough. Color: Spinach Green, Plate No. 75 (K), shaded with Moss Green, Plate No. 76 (K).

*Thorns.*—None.

*Hairs.*—Few. Color: Pure White, Plate No. 1 (K).

THE FLOWER

Blooming habit: Free and continuous in greenhouse with abundant bloom production.

Borne: One to four on a medium strong stem; may be disbudded for commercial use.

Arrangement: In regular clusters.

Form: Full and high centered at first, with petals tightly rolled inward; the petals becoming loosely rolled outward at maturity.

Size: When fully opened, small.

*Diameter.*—About 2 to 2½ inches.

Petalage: Double, with from seventeen to twenty-five petals regularly arranged.

*Shape.*—Outside, Intermediate and Inside Petals: Oval with obtuse apex and rounded base.

*Texture.*—Moderately thick.

*Aspect.*—Velvety inside and satiny outside.

*Color.*—All Petals: Nearest color — Cardinal Red, 822/1 (HCC), on both outside and inside surfaces of both newly-opened and three days opened blooms. The colors may be modified by being bordered, margined, pencilled, striped, dotted, blotched, shaded, washed, or tinted, with other colors.

Persistence: The petals hang on and dry.

Lasting quality: From seven to ten days kept at living room temperatures in December.

REPRODUCTIVE ORGANS

Stamens: Many in number, arranged regularly about the pistils.

*Filaments.*—Short, many with anthers. Color: Pure White, Plate No. 1 (K).

*Anthers.*—Size: Small, all open at once and at various times from season to season. Color: Buff, Plate No. 90 (K).

*Pollen.*—Quantity: Moderate. Color: Buff, Plate No. 90 (K).

Pistils:

*Number.*—Medium.

*Styles.*—Uneven, of medium length, medium heavy and bunched. Color: Chrysanthemum Crimson, 824/3 (HCC).

*Stigma.*—Color: Buff, Plate No. 90 (K).

Ovularies: All encased in the calyx.

Hips: None.

This new variety possesses the good characteristics of its seed parent 'Cindy'; however, with an improvement in winter greenhouse productivity. It also possesses the good attributes of its pollen parent 'Sassy' but with more petalage and increase of flower size.

I claim:

1. The new and distinctive red rose plant and parts thereof, substantially as herein shown and described, characterized by the overall cardinal red flower coloration, its vigorous growth habit, and its free and continuous blooming in greenhouse culture.

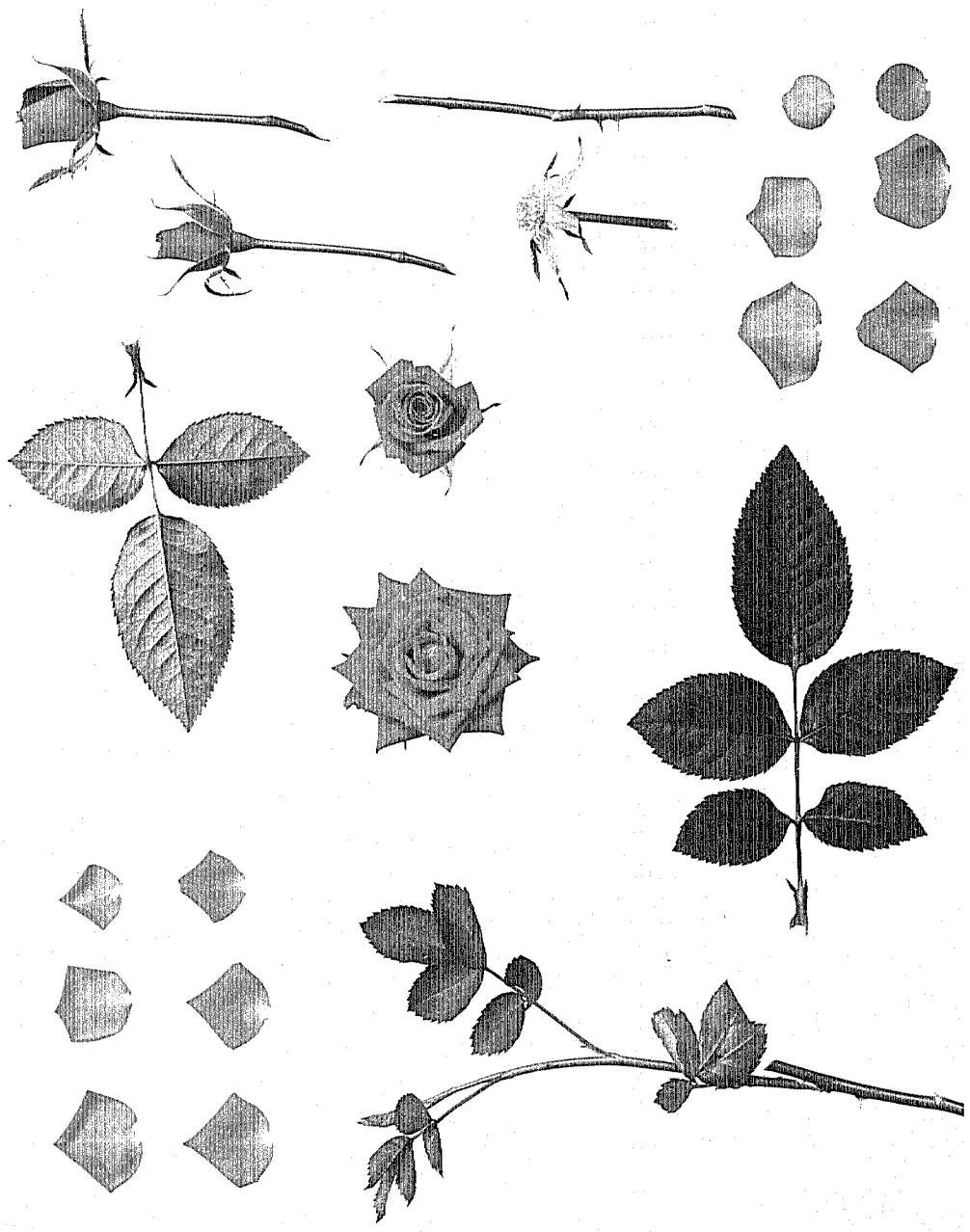

* * * * *